(12) United States Patent
Kapranov et al.

(10) Patent No.: US 7,053,265 B2
(45) Date of Patent: May 30, 2006

(54) APPLICATION OF BI-DIRECTIONAL PROMOTERS FOR MODIFICATION OF GENE EXPRESSION

(75) Inventors: Philipp Kapranov, Sunnyvale, CA (US); Krzysztof Szczyglowski, London (CA)

(73) Assignee: The Board of Trustees Operating Michigan State University, East Lansing, MI (US)

( * ) Notice: Subject to any disclaimer, the term of this patent is extended or adjusted under 35 U.S.C. 154(b) by 364 days.

(21) Appl. No.: 09/969,263

(22) Filed: Oct. 1, 2001

(65) Prior Publication Data

US 2002/0108142 A1    Aug. 8, 2002

Related U.S. Application Data

(60) Provisional application No. 60/237,325, filed on Oct. 2, 2000.

(51) Int. Cl.
| | | |
|---|---|---|
| C07H 21/02 | (2006.01) | |
| C12N 15/87 | (2006.01) | |
| C12N 15/00 | (2006.01) | |
| A01H 5/00 | (2006.01) | |
| C12P 21/06 | (2006.01) | |

(52) U.S. Cl. .................. 800/69.1; 435/320.1; 435/419; 800/278; 536/24.1; 536/23.5; 536/23.6

(58) Field of Classification Search ............... 536/24.1, 536/23.5, 23.6; 435/69.1, 320.1; 800/278
See application file for complete search history.

(56) References Cited

U.S. PATENT DOCUMENTS

| | | | |
|---|---|---|---|
| 4,876,197 A | 10/1989 | Burke et al. | |
| 4,880,734 A | 11/1989 | Burke et al. | |
| 5,625,136 A | 4/1997 | Koziel et al. | |
| 5,646,012 A * | 7/1997 | Fleer et al. ................. | 435/69.1 |
| 5,952,195 A | 9/1999 | Nacken et al. | |
| 6,083,717 A | 7/2000 | Madzak et al. | |
| 6,118,049 A | 9/2000 | Bestwick et al. | |

OTHER PUBLICATIONS

Menne, S et al. Expression studies with the bidirectional pcbAB-pcbC promoter region from Acremonium chrysogenum using reporter gene fusions. Appl. Microbio. Biotechnol. (1994) 42:57-66.*
Ryan et al. The genes encoding mammalian chaperonin 60 and chaperonin 10 are linked head-to-head and share a bidirectional promoter. Gene (1997) 196:9-17.*
Brayton et al. Two Genes for de Novo Purine Nucleotide Synthesis on Human Chromsome 4 Are Closely Linked and Divergently Transcribed. JBC (1994) 268: 5313-5321.*
Keddie et al. A seed-specific Brassica napus oleosin promoter interacts with a G-box-specific protein and may be bi-directional. Plant Molecular Biology (1994) 24: 3277-340.*
Szczyglowski et al., Plant Cell, 6:317 [1994].
Ramlow et al., Plant J., 4:577 [1993].
Hudspeth and Grula, Plant Molec. Biol., 12:579 [1989].
Guifoyle et al., Plant Physiol., 118:341 [1998].
Guifoyle et al., Cell. Mol. Life Sci., 54:619 [1998].
Goldstein and Doi, Biotechnol Ann. Rev., 1:105 [1995].
Menendez et al., Rev Latinoam Microbiol., 40:136 [1998].
Madzak et al., J Mol Microbiol Biotechnol., 2:207 [2000].
Arakawa et al., Transgenic Research 6:403 [1997].
Keddie et al., Plant Mol. Biol., 24:327 [1994].
Leung et al., Mol. Gen. Genet., 230:463 [1991].
Kapranov et al., Plant Physiol., 113:1081 [1997].
Szczyglowski et al., Plant Physiol., 114:1335 [1997].
Jarvis et al., Int. J. Syst. Bact., 32:378 [1982].

(Continued)

*Primary Examiner*—Terry McKelvey
*Assistant Examiner*—Maria Marvich
(74) *Attorney, Agent, or Firm*—Medlen & Carroll, LLP

(57) ABSTRACT

The present invention provides a novel bi-directional promoter. The present invention further provides methods of producing proteins of interest and methods of controlling gene expression using the bi-directional promoter. The present invention also provides methods of expressing one or more proteins of interest from a novel bi-directional promoter of the present invention. The present invention thus provides improved methods of regulating gene expression in plants or other organisms and expressing one or more proteins concurrently in a variety of cell types.

20 Claims, 1 Drawing Sheet

OTHER PUBLICATIONS

Pankhurst et al., J. Gen. Microbiol., 132:2321 [1986].

Hagstrom et al., Blood, 95:2536 [2000].

Endl et al. PNAS 96:1445 [1999].

Birchler et al., Curr. Opin. in Genetics and Development 10:211 [2000].

Jorgensen et al., "Do unintended antisense transcripts contribute to sense cosuppression in plants?" TIGs 15:11 [1999].

Fujita et al., "Nucleic acid-binding properties and subcellular localization of the 3a protein of brome mosaic bromovirus," J. Gen. Virol. 79:1273 [1998].

Okanami et al., "Characterization of a DEAD box ATPase/RNA helicase protein of *Arabidopsis thaliana*," Nuc. Acid. Res. 26:2638 [1998].

Stam et al., "Distinct features of post-transcriptional gene silencing by antisense transgenes in single copy and inverted T-DNA repeat loci," The Plant journal 21:27 [2000].

Suen and Goss, "Transcription of BRCAI is dependent of the formation of a specific protein-DNA complexes on the minimal BRCAI Bi-directional promoter," J. Biol. Chem. 274:31297 [1999].

Huang et al., "TAT elements direct bi-directional transcription by RNA polymcrases II and III," Nuc. Acid. Res. 24:1158 [1996].

Xie et al., "Bidirectionization of polar promoters in plants," Nature Biotech., 19:677 [2001].

Zuo and Chua, Curr. Opin. Biotechnol., 11:146 (2000).

\* cited by examiner

APPLICATION OF BI-DIRECTIONAL PROMOTERS FOR MODIFICATION OF GENE EXPRESSION

This application claims priority to co-pending U.S. provisional application Ser. No. 60/237,325 filed Oct. 2, 2000, which is herein incorporated by reference in its entirety.

This invention was made in part during work partially supported by the U.S. government under DOE grant No. 61-3200. The government may have certain rights in the invention.

FIELD OF THE INVENTION

The present invention provides a novel bi-directional promoter. The present invention further provides methods of producing proteins of interest and methods of controlling gene expression using the bi-directional promoter.

BACKGROUND OF THE INVENTION

Traditional methods for the modification of gene expression in plants are characterized as "forward" and "reverse" genetic approaches. "Forward" genetic approaches include classical genetic analysis of naturally occurring or induced genetic variance in a plant or other organism. "Reverse" genetic approaches rely on the inactivation or modification of a specific gene.

Forward genetic approaches such as classical genetic techniques are limited by the available methods of detecting naturally occurring mutations and by methods of inducing mutations. Such techniques do not allow the researcher to target a specific gene for mutation but instead rely on the time-consuming process of screening large numbers of mutant plants or other organisms.

Available reverse genetic approaches require prior knowledge of the gene sequence. There are no reliable methods of gene replacement via homologous recombination available for use in higher plants. Methods of gene modification in plants instead rely upon a variety of alternative methods including insertional mutagenesis using "active" and "inactive" T-DNA species, as well as transposon mutagenesis. Additional methods include the production of sense or antisense transcripts using tissue-specific or constitutive regulatory elements.

The currently available techniques for reverse genetics in plants have many drawbacks. The methods are laborious and typically require generation and screening of large populations of transgenic plants. Further, these methods are not suitable for many recalcitrant plant species, including major crop species, where obtaining a large number of transgenic plants is difficult, impractical, or simply impossible. The art is thus in need of efficient, reliable methods for modifying gene expression in plants.

SUMMARY OF THE INVENTION

The present invention provides a novel bi-directional promoter. The present invention further provides methods of producing proteins of interest and methods of controlling gene expression using the bi-directional promoter.

The present invention provides a composition comprising at least a portion of an isolated *Lotus japonicus* PLP-IV promoter nucleic acid sequence. In some embodiments, the *Lotus japonicus* PLP-IV promoter nucleic acid sequence comprises SEQ ID NO:4. In other embodiments, the *Lotus japonicus* PLP-IV promoter nucleic acid sequence comprises sequences that hybridize to at least a portion of SEQ ID NO:4 under conditions of low stringency. In some embodiments, the portion comprises one or more sequences selected from the group consisting of the complement of nucleotides 83–91 of SEQ ID NO: 4, the complement of nucleotides 49–53 of SEQ ID NO: 4, the complement of nucleotides 11–119 of SEQ ID NO: 4, the complement of nucleotides 173–183 of SEQ ID NO: 4, nucleotides 286–294 of SEQ ID NO: 4, nucleotides 532–537 of SEQ ID NO: 4, and nucleotides 397–405 of SEQ ID NO: 4. In some embodiments, the promoter is a bi-directional promoter. In yet other embodiments, the present invention provides a computer readable medium encoding a representation of the nucleic acid sequence of an isolated *Lotus japonicus* PLP-IV promoter.

The present invention also provides a vector comprising the above described composition. In some embodiments, the *Lotus japonicus* PLP-IV promoter nucleic acid sequence comprises SEQ ID NO:4. In other embodiments, the *Lotus japonicus* PLP-IV promoter nucleic acid sequence comprises sequences that hybridize to at least a portion of SEQ ID NO:4 under conditions of low stringency. In some embodiments, the portion comprises one or more sequences selected from the group consisting of the complement of nucleotides 83–91 of SEQ ID NO: 4, the complement of nucleotides 49–53 of SEQ ID NO: 4, the complement of nucleotides 11–119 of SEQ ID NO: 4, the complement of nucleotides 173–183 of SEQ ID NO: 4, nucleotides 286–294 of SEQ ID NO: 4, nucleotides 532–537 of SEQ ID NO: 4, and nucleotides 397–405 of SEQ ID NO: 4. In some embodiments, the promoter is a bi-directional promoter. In yet other embodiments, the promoter is operably linked to a reporter gene. In still further embodiments, the present invention provides a computer readable medium encoding a representation of the nucleic acid sequence of the vector. In some embodiments, the present invention provides a plant cell transformed with the vector. In some embodiments, the present invention provides a differentiated dicotyledonous plant comprising the plant cell. In other embodiments, the present invention provides a differentiated monocotyledonous plant comprising the plant cell.

The present invention further provides a vector comprising two nucleic acid sequences in opposite orientation, wherein the two nucleic acid sequences are separated by at least a portion of an isolated *Lotus japonicus* PLP promoter nucleic acid sequence. In some embodiments, the *Lotus japonicus* PLP-IV promoter nucleic acid sequence comprises SEQ ID NO:4. In other embodiments, the *Lotus japonicus* PLP-IV promoter nucleic acid sequence comprises sequences that hybridize to at least a portion of SEQ ID NO:4 under conditions of low stringency. In some embodiments, the portion comprises one or more sequences selected from the group consisting of the complement of nucleotides 83–91 of SEQ ID NO: 4, the complement of nucleotides 49–53 of SEQ ID NO: 4, the complement of nucleotides 11–119 of SEQ ID NO: 4, the complement of nucleotides 173–183 of SEQ ID NO: 4, nucleotides 286–294 of SEQ ID NO: 4, nucleotides 532–537 of SEQ ID NO: 4, and nucleotides 397–405 of SEQ ID NO: 4. In some embodiments, the promoter is a bi-directional promoter. In yet other embodiments, the promoter is operably linked to a reporter gene. In still further embodiments, the present invention provides a computer readable medium encoding a representation of the nucleic acid sequence of the vector. In some embodiments, the present invention provides a plant cell transformed with the vector. In some embodiments, the present invention provides a differentiated dicotyledonous plant comprising the plant cell. In other embodiments, the present invention provides a differentiated monocotyledonous plant comprising the plant cell.

The present invention additionally provides a transgenic plant comprising a transgene, wherein the transgene comprises a vector comprising two nucleic acid sequences in opposite orientation, wherein the two nucleic acid sequences are separated by at least a portion of an isolated *Lotus japonicus* PLP promoter nucleic acid sequence. In some embodiments, the *Lotus japonicus* PLP-IV promoter nucleic acid sequence comprises SEQ ID NO:4. In other embodiments, the *Lotus japonicus* PLP-IV promoter nucleic acid sequence comprises sequences that hybridize to at least a portion of SEQ ID NO:4 under conditions of low stringency. In some embodiments, the portion comprises one or more sequences selected from the group consisting of the complement of nucleotides 83–91 of SEQ ID NO: 4, the complement of nucleotides 49–53 of SEQ ID NO: 4, the complement of nucleotides 11–119 of SEQ ID NO: 4, the complement of nucleotides 173–183 of SEQ ID NO: 4, nucleotides 286–294 of SEQ ID NO: 4, nucleotides 532–537 of SEQ ID NO: 4, and nucleotides 397–405 of SEQ ID NO: 4. In yet other embodiments, the promoter is a bi-directional promoter. In still further embodiments, the promoter is operably linked to a reporter gene.

The present invention additionally provides a method comprising: providing a cell; a vector comprising two nucleic acid sequences in opposite orientation, wherein the two nucleic acid sequences are separated by a *Lotus japonicus* PLP promoter nucleic acid sequence; and transforming the cell with the vector under conditions such that the two nucleic acid sequences are transcribed to produce two complementary RNA sequences. In some embodiments, the *Lotus japonicus* PLP-IV promoter nucleic acid sequence comprises SEQ ID NO:4. In other embodiments, the *Lotus japonicus* PLP-IV promoter nucleic acid sequence comprises sequences that hybridize to at least a portion of SEQ ID NO:4 under conditions of low stringency. In still further embodiments, the portion comprises one or more sequences selected from the group consisting of the complement of nucleotides 83–91 of SEQ ID NO: 4, the complement of nucleotides 49–53 of SEQ ID NO: 4, the complement of nucleotides 11–119 of SEQ ID NO: 4, the complement of nucleotides 173–183 of SEQ ID NO: 4, nucleotides 286–294 of SEQ ID NO: 4, nucleotides 532–537 of SEQ ID NO: 4, and nucleotides 397–405 of SEQ ID NO: 4. In some embodiments, the promoter is a bi-directional promoter. In some embodiments, the cell is a plant cell. In some embodiments, the plant cell is part of a plant.

The present invention also provides a method of regulating expression of a gene of interest comprising: providing a cell comprising a gene of interest; a vector comprising two nucleic acid sequences in opposite orientation, wherein the two nucleic acid sequences are separated by a *Lotus japonicus* PLP promoter nucleic acid sequence; and transforming the cell with the vector under conditions such that the level of expression of the gene of interest is altered relative to the level of expression of the gene in the absence of the vector. In some embodiments, the *Lotus japonicus* PLP-IV promoter nucleic acid sequence comprises SEQ ID NO:4. In other embodiments, the *Lotus japonicus* PLP-IV promoter nucleic acid sequence comprises sequences that hybridize to at least a portion of SEQ ID NO:4 under conditions of low stringency. In some embodiments, the portion comprises one or more sequences selected from the group consisting of the complement of nucleotides 83–91 of SEQ ID NO: 4, the complement of nucleotides 49–53 of SEQ ID NO: 4, the complement of nucleotides 11–119 of SEQ ID NO: 4, the complement of nucleotides 173–183 of SEQ ID NO: 4, nucleotides 286–294 of SEQ ID NO: 4, nucleotides 532–537 of SEQ ID NO: 4, and nucleotides 397–405 of SEQ ID NO: 4. In some embodiments, the promoter is a bi-directional promoter. In some embodiments, the cell is a plant cell. In some embodiments, the plant cell is part of a plant.

In further embodiments, the present invention provides a method of producing one or more proteins comprising: providing a vector comprising two genes of interest in opposite orientation, wherein said two genes of interest are separated by a *Lotus japonicus* PLP-IV promoter nucleic acid sequence; and a host cell; and transforming the host cell with the vector under conditions such that the two proteins are produced. In some embodiments, the *Lotus japonicus* PLP-IV promoter nucleic acid sequence comprises SEQ ID NO: 4. In other embodiments, the *Lotus japonicus* PLP-IV promoter nucleic acid sequence comprises sequences that hybridize to at least a portion of SEQ ID NO:4 under conditions of low stringency. In some embodiments, the portion comprises one or more sequences selected from the group consisting of the complement of nucleotides 83–91 of SEQ ID NO: 4, the complement of nucleotides 49–53 of SEQ ID NO: 4, the complement of nucleotides 11–119 of SEQ ID NO: 4, the complement of nucleotides 173–183 of SEQ ID NO: 4, nucleotides 286–294 of SEQ ID NO: 4, nucleotides 532–537 of SEQ ID NO: 4, and nucleotides 397–405 of SEQ ID NO: 4. In some embodiments, the promoter is a bi-directional promoter. In some embodiments, the host cell is a plant cell. In some embodiments, the plant cell is part of a plant. In some embodiments, the host cell is selected from the group consisting of a bacterial cell, a yeast cell, an insect cell, and a mammalian cell.

The present invention further provides a method of generating a bi-directional promoter, comprising providing a unidirectional promoter comprising a first minimal promoter; and a second minimal promoter, wherein said second minimal promoter is in the opposite orientation as said first minimal promoter; and fusing said second minimal promoter to the 5' end of said first minimal promoter to generate a bi-directional promoter. In some embodiments, the first and second minimal promoters are the same. In other embodiments, the minimal promoters are *Lotus japonicus* PLP-IV minimal promoters. In some embodiments, the *Lotus japonicus* PLP-IV minimal promoter comprises one or more sequences selected from the group consisting of the complement of nucleotides 83–91 of SEQ ID NO: 4, the complement of nucleotides 49–53 of SEQ ID NO: 4, the complement of nucleotides 11–119 of SEQ ID NO: 4, the complement of nucleotides 173–183 of SEQ ID NO: 4, nucleotides 286–294 of SEQ ID NO: 4, nucleotides 532–537 of SEQ ID NO: 4, and nucleotides 397–405 of SEQ ID NO: 4.

DEFINITIONS

Figure 1:
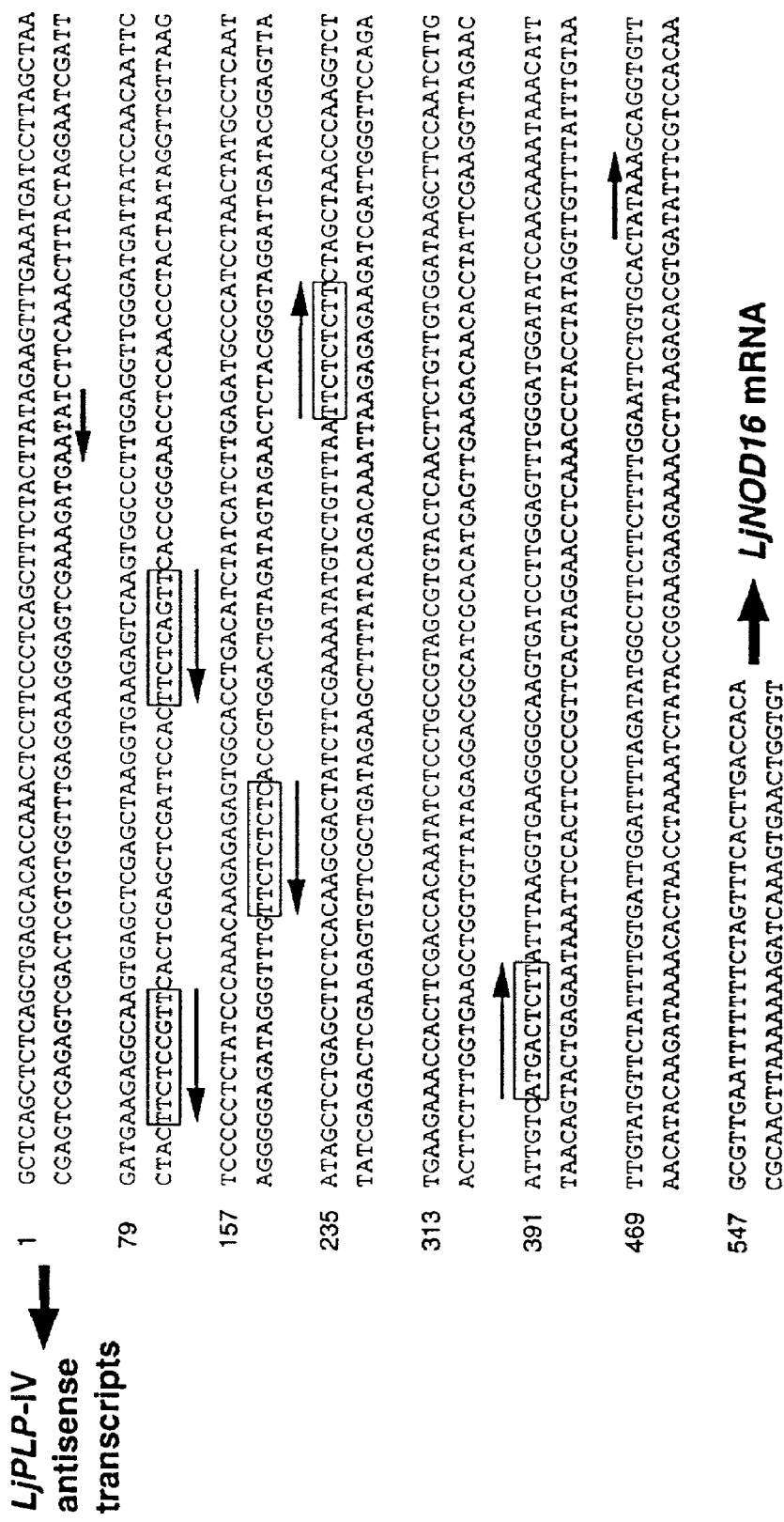
FIG. 1 shows the nucleic acid sequence of SEQ ID NO: 4.

To facilitate an understanding of the invention, a number of terms are defined below.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent to mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "homology" and "percent identity" when used in relation to nucleic acids refers to a degree of complementarity. There may be partial homology (i.e., partial identity) or complete homology (i.e., complete (100%) identity). As used herein, a partially complementary sequence is one that at least partially inhibits (e.g., greater than 10% inhibition) a completely complementary sequence from hybridizing to a target nucleic acid sequence and is referred to using the functional term "substantially homologous." The inhibition of hybridization of the completely complementary sequence to the target sequence may be examined using a hybridization assay (Southern or Northern blot, solution hybridization and the like) under conditions of low to high stringency. A substantially homologous sequence (e.g., one having greater than 80% identity) or probe (i.e., an oligonucleotide which is capable of hybridizing to another oligonucleotide of interest) will compete for and inhibit (e.g., greater than 50% inhibition) the binding (i.e., the hybridization) of a completely homologous sequence to a target sequence under conditions of low to high stringency. This is not to say that conditions of low stringency are such that non-specific binding is permitted; low stringency conditions require that the binding of two sequences to one another be a specific (i.e., selective) interaction, although some mismatches are permitted. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize (i.e., it is the complement of) the single-stranded nucleic acid sequence under conditions of low to high stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the Tm of the formed hybrid, and the G:C ratio within the nucleic acids. A single molecule that contains pairing of complementary nucleic acids within its structure is said to be "self-hybridized." As used herein, the term "$T_m$" is used in reference to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl (See e.g., Anderson and Young, Quantitative Filter Hybridization, *in Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5× SSPE (43.8 g/l NaCl, 6.9 g/l NaH$_2$PO$_4$H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5× SSPE (43.8 g/l NaCl, 6.9 g/l NaH$_2$PO$_4$H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5× SSPE (43.8 g/l NaCl, 6.9 g/l NaH$_2$PO$_4$H$_2$O and 1.85 µg/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5× SSPE, 0.1% SDS at 42° C. when a probe of about 500 nucleotides in length is employed.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al, Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled nucleic acid probe (e.g., DNA or RNA) to detect DNA species complementary to the probe used. The DNA may be cleaved with restriction enzymes prior to electrophoresis and transfer to solid support. Southern blots are a standard tool of molecular biologists (Sambrook et al., Molecular Cloning: A Laboratory Manual, Cold Spring Harbor Press, NY, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al., supra, pp 7.39–7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or PVDF membrane. The immobilized proteins are then exposed to antibodies with reactivity against an antigen of interest. The binding of the antibodies may be detected by various methods, including the use of radiolabeled antibodies.

The term "antigenic determinant" as used herein refers to that portion of an antigen (i.e., an epitope) that makes contact with a particular antibody . When a protein or fragment of a protein is used to immunize a host animal, numerous regions of the protein may induce the production of antibodies that bind specifically to a given region or three-dimensional structure on the protein; these regions or structures are referred to as "antigenic determinants".

The term "nucleotide sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation. Antisense RNA may be produced by any method, including synthesis by cloning the gene(s) of interest in a reverse orientation under the control of a promoter and transcribed. This transcribed strand can combine with a sense or mRNA to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein, the term "dsRNA" refers to two complementary RNA molecules that have annealed to one-another to form a double stranded RNA molecule. The two strands may comprise the "sense" and "antisense" RNAs of a gene, or alternatively, may comprise complementary RNA molecule that do not code for a gene.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic sequences of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "genome" refers to the genetic material (e.g., chromosomes) of an organism.

As used herein, the term "heterologous gene" refers to a gene encoding a factor that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed). The coding sequence of the heterologous gene is operatively linked to an expression control sequence. Generally a heterologous gene is first placed into a vector.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain. The DNA or RNA sequence thus codes for the amino acid sequence.

A gene may produce multiple RNA species that are generated by differential splicing of the primary RNA transcript. RNA species that are splice variants of the same gene will contain regions of sequence identity or complete homology (representing the presence of the same exon or portion of the same exon on both RNAs) and regions of complete non-identity (for example, representing the presence of exon "A" on RNA 1 wherein RNA 2 contains exon "B" instead). Because the two RNAs contain regions of sequence identity they will both hybridize to a probe derived from the entire gene or portions of the gene containing sequences found on both RNAs; the two splice variants are therefore substantially homologous to such a probe and to each other.

As used herein, the term "altered level of gene expression" as used in reference to the comparison of the level of expression of a gene in the presence and absence of a vector containing a promoter of the present invention (e.g., the LjPLP-IV promoter) refers to a measurable or observable change in the level of expression of a gene (e.g., measured through a suitable assay such as a "northern blot" or through an observable change in phenotype).

As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the term "integrated" refers to a vector that is stably inserted into the genome (i.e., into a chromosome) of a host cell.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, RNA export elements, internal ribosome entry sites, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al, Science 236:1237 [1987]). Promoter and enhancer elements have been isolated from a variety of eukaryotic sources including genes in plant, yeast, insect and mammalian cells, and viruses (analogous control elements, i.e., promoters, are also found in prokaryotes). The selection of a particular promoter and enhancer depends on what cell type is to be used to express the protein of interest.

As used herein, the term "bi-directional promoter" refers to a "promoter" capable of directing transcription in both the forward and reverse orientations. "Bi-directional promoters" (e.g., the LjPLP-IV promoter) can direct the transcription of two transcripts placed in either orientation (i.e., downstream or upstream) of the promoter simultaneously (e.g., the "sense" and "antisense" strands of a gene). In other words, a "bi-directional promoter" directs transcription from either strand of the "promoter" region. A diagram of transcripts directed by one "bi-directional promoter" (e.g., the LjPLP-IV promoter) is shown in FIG. 1.

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques such as cloning and recombination) such that transcription of that gene is directed by the linked enhancer/promoter.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

As used herein, the term "functional equivalents," when used in reference to a promoter of interest (e.g., the LjPLP-IV promoter) refers to a promoter capable of being substituted for the promoter of interest and retaining the function, although not necessarily with the same strength, of the promoter of interest (e.g., the ability to direct bi-directional transcription). Functional equivalents are able to direct bi-direction transcription with a strength of at least 50%, preferably with a strength of at least 75%, and more preferably with a strength of at least 90% of the LjPLP-IV promoter of SEQ ID NO:4. Promoter strength may be measured by any suitable method, including but not limited to the reporter gene assay described in Example 2. In some embodiments, "functional equivalents" comprise sequence variants or homologs that hybridize to the LjPLP-IV promoter under conditions of varying stringency and are able to direct bi-directional transcription as described above.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, etc.). In contrast, a "regulatable" promoter is one that is capable of directing a level of transcription of an operably linked nucleic acid sequence in the presence of a stimulus (e.g., heat shock, chemicals, etc.), which is different from the level of transcription of the operably linked nucleic acid sequence in the absence of the stimulus.

The presence of "splicing signals" on an expression vector often results in higher levels of expression of the recombinant transcript. Splicing signals mediate the removal of introns from the primary RNA transcript and consist of a splice donor and acceptor site (Sambrook et al., *Molecular Cloning: A Laboratory Manual,* 2nd ed., Cold Spring Harbor Laboratory Press, New York [1989], pp. 16.7–16.8). A commonly used splice donor and acceptor site is the splice junction from the 16S RNA of SV40.

As used herein, the term "transgene" refers to a heterologous gene that is integrated into the genome of an organism (e.g., a plant) and that is transmitted to progeny of the organism during sexual reproduction.

As used herein, the term "transgenic organism" refers to an organism (e.g., a plant) that has a transgene integrated into its genome and that transmits the transgene to its progeny during sexual reproduction.

As used herein, the term "host cell" refers to any eukaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including, but not limited to plant (e.g., protoplast), mammalian, yeast, bacterial, and insect cells.

Where "amino acid sequence" is recited herein to refer to an amino acid sequence of a naturally occurring protein molecule, "amino acid sequence" and like terms, such as "polypeptide or protein" are not meant to limit the amino acid sequence to the complete, native amino acid sequence associated with the recited protein molecule.

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a polypeptide of interest includes, by way of example, such nucleic acid in cells ordinarily expressing the polypeptide where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "coding region" when used in reference to a structural gene refers to the nucleotide sequences that encode the amino acids found in the nascent polypeptide as a result of translation of a mRNA molecule. The coding region is typically bounded, in eukaryotes, on the 5' side by the nucleotide triplet "ATG" that encodes the initiator methionine and on the 3' side by one of the three triplets which specify stop codons (i.e., TAA, TAG, TGA).

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (e.g., 4, 5, 6, 7, ... n–1).

As used herein, the term "at least a portion of," when used in reference to a promoter of the present invention (e.g., the LjPLP-IV promoter) refers to any portion of the promoter, that is capable of acting as a "functional equivalent" of the promoter, either alone, or in combination with "sequences" of other promoters (e.g., sub-portions of a promoter or chimeric sequences that are functionally equivalent). Functional equivalents are able to direct bi-direction transcription with a strength of at least 50%, preferably with a strength of at least 75%, and more preferably with a strength of at least 90% of the LjPLP-IV promoter of SEQ ID NO:4. Promoter strength may be measured by any suitable method, including but not limited to the reporter gene assay described in Example 2. In some embodiments, the portions comprise minimal promoter sequences in combination with cis elements (e.g., including but not limited to, one or more sequences selected from the group consisting of the complement of nucleotides 83–91 of SEQ ID NO: 4, the complement of nucleotides 49–53 of SEQ ID NO: 4, the complement of nucleotides 11–119 of SEQ ID NO: 4, the complement of nucleotides 173–183 of SEQ ID NO: 4, nucleotides 286–294 of SEQ ID NO: 4, nucleotides 532–537 of SEQ ID NO: 4, and nucleotides 397–405 of SEQ ID NO: 4).

As used herein, the term "minimal promoter" refers to the region of the promoter where an RNA polymerase and associated binding proteins (e.g., including but not limited to, TATA binding protein and TATA binding protein associated factors) In some embodiments, the minimal promoter is a TATA box. In some embodiments of the present invention, the minimal promoter comprises one or more sequences selected from the group consisting of the complement of nucleotides 83–91 of SEQ ID NO: 4, the complement of nucleotides 49–53 of SEQ ID NO: 4, the complement of nucleotides 11–119 of SEQ ID NO: 4, the complement of nucleotides 173–183 of SEQ ID NO: 4, nucleotides 286–294 of SEQ ID NO: 4, nucleotides 532–537 of SEQ ID NO: 4, and nucleotides 397–405 of SEQ ID NO: 4.

The term "recombinant protein" or "recombinant polypeptide" as used herein refers to a protein molecule that is expressed from a recombinant DNA molecule.

As used herein the term "portion" when in reference to a protein (as in "a portion of a given protein") refers to fragments of that protein. The fragments may range in size from four amino acid residues to the entire amino acid sequence minus one amino acid (e.g., 4, 5, 6, 7, ... n–1).

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

A "composition comprising a given polynucleotide sequence" as used herein refers broadly to any composition containing the given polynucleotide sequence. Compositions comprising polynucleotide sequences or fragments thereof may be employed as hybridization probes. In this case, the polynucleotide sequences are typically employed in an aqueous solution containing salts (e.g., NaCl), detergents (e.g., SDS), and other components (e.g., Denhardt's solution, dry milk, salmon sperm DNA, etc.).

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

The term "test compound" refers to any chemical entity, pharmaceutical, drug, and the like that can be used to treat or prevent a disease or infection, or otherwise alter the physiological or cellular status of a sample (e.g., a plant). Test compounds comprise both known and potential therapeutic compounds. A test compound can be determined to be therapeutic by screening using the screening methods of the present invention. A "known therapeutic compound" refers to a therapeutic compound that has been shown (e.g., through expression or administration to a plant) to be effective in such treatment or prevention. In other words, a known therapeutic compound is not limited to a compound efficacious in the treatment of pathological conditions such as disease, viral infection, or attack by insects.

As used herein, the term "sample" is used in its broadest sense. In one sense it can refer to a tissue sample. In another sense, it is meant to include a specimen or culture obtained from any source, as well as biological. Biological samples may be obtained from animals or plants and encompass fluids, solids, tissues, and gases. Biological samples include, but are not limited to plant tissues, cells, or extracts. These examples are not to be construed as limiting the sample types applicable to the present invention.

DETAILED DESCRIPTION OF THE INVENTION

The present invention provides bi-directional promoters for use in regulation of gene expression in plants and other organisms. The present invention also provides methods and compositions for the expression of one or more polypeptides (e.g., two subunits of a multi-subunit protein) from the same promoter construct. The description below provides specific, but not limiting, illustrative examples of uses of the bi-directional promoters disclosed herein.

I. LjPLP-IV Promoter

In some embodiments, the present invention provides compositions comprising novel bi-directional promoter from *Lotus japonicus* (LjPLP-IV promoter). In some embodiments, the present invention provides the nucleic acid sequence of the *Lotus japonicus* PLP-IV intron-born promoter (LjPLP-IV promoter; SEQ ID NO:4; FIG. 1), and functional equivalents. The LjPLP-IV promoter is contained in intron 10 of the LjPLP-IV gene. The putative promoter was defined as a 581-bp fragment located between the sense and antisense transcripts. Analysis of the promoter region revealed the presence of several potential regulatory elements (See FIG. 1). Two TATA box-like sequences were found approximately 40 bp upstream of the longest sense and antisense cDNAs. Furthermore, a number of DNA sequence motifs, showing high similarity to nodulin gene consensus sequence (5'-TTGTCTCTT-3'; SEQ ID NO:5) were present within this putative promoter sequence (FIG. 1; Szczyglowski et al., Plant Cell, 6:317 [1994]). These motifs, especially the CTCTT core sequences, have been shown to be required for nodule infected-cell-specific expression of late nodulin genes, such as the leghemoglobin gene (Ramlow et al., Plant J., 4:577 [1993]; Szczyglowski et al., Plant Cell, 6:317 [1994]). Both the nodulin-box motifs and the TATA box motifs are located on both strands of the promoter sequence, coinciding with the presumed orientation of the bi-directional gene transcription (FIG. 1).

The presence of the bi-directional LjPLP-IV promoter in the LjPLP-IV gene was confirmed by the production of transgenic plants (See Example 2). In this illustrative example, a 581-bp fragment, encompassing the predicted promoter region of the intron, was fused in both orientations to the coding region of a uidA reporter gene encoding -glucuronidase (GUS). Thus, one construct contained the GUS coding region fused to the promoter it its forward orientation and one construct contained the GUS coding region fused to the promoter in its reverse orientation. The vectors were transformed into lotus and expression was measured by GUS staining. The intron-contained promoter sequence was found to be capable of activating the reporter gene expression in an orientation-independent manner.

In some embodiments, the present invention provides the LjPLP-IV promoter sequence shown in SEQ ID NO:4. In other embodiments, the present invention provides a sequence that hybrizides to SEQ ID NO:4 (e.g., under conditions of low, medium, or high stringency). Such sequences are tested for functional equivalence to SEQ ID NO:4 using the assay described in Example 2.

In yet other embodiments, the present invention provides a sequence containing a portion of SEQ ID NO:4. Portions comprising function equivalents of the LjPLP-IV promoter can be identified using any suitable method, including, but not limited to those described below for the regulation of gene expression or expression of proteins of interest. Alternatively, functional equivalents can be determined by attaching portions (e.g., truncations) of the LjPLP-IV promoter to a reporter construct (e.g., GUS) and expression measured using any suitable assay (e.g., that described in Example 2 below).

In some embodiments, the present invention provides chimeras comprising a portion of the LjPLP-IV promoter of SEQ ID NO:4. In some embodiments, the chimeric constructs provide additional regulatory sequences that direct expression to a specific tissue. In some embodiments, these sequences are substituted for the nodulin-box motifs described above. For example, suitable sequences include, but are not limited to, sequences derived from the maize PEPC promoter from the phosphoenol carboxylase gene that direct expression in green tissue (Hudspeth and Grula, Plant Molec. Biol., 12:579 [1989]); elements of T1 promoters that direct root specific expression (EP 0 452 269; herein incorporated by reference); hormone response elements (e.g., auxin response elements (AuxREs), Guiltoyle et al., Plant Physiol., 118:341 [1998]; Guiltoyle et al., Cell. Mol. Life Sci., 54:619 [1998]; and elements of the stem specific promoter from the maize trpA gene (U.S. Pat. No. 5,625, 136; herein incorporated by reference). The present invention is not limited to elements of the tissue-specific promoters described herein. One skilled in the art recognizes that other suitable elements may be utilized. The present invention is not limited to promoter sequences for use in plants. Indeed, it is contemplated that the LjPLP-IV promoter can serve as a basis for chimeric bi-directional promoters active in organisms other than plants.

Hybrid (e.g., chimeric) promoters containing a portion of a LjPLP-IV promoter (e.g., SEQ ID NO:4) may be constructed using any suitable technique. For example, hybrid promoters have been designed for use in bacteria (See e.g., Goldstein and Doi RH, Biotechnol Annu Rev., 1:105 [1995]; Menendez et al., Rev Latinoam Microbiol., 40:136 [1998]); yeast (See e.g., Madzak et al., J Mol Microbiol Biotechnol., 2:207 [2000]; U.S. Pat. No. 6,083,717; herein incorporated by reference); gene therapy in animal models (See e.g., Hagstrom et al., Blood, 95:2536 [2000]); and plants (See e.g., Zuo and Chua, Curr. Opin. Biotechnol., 11:146 [2000]; U.S. Pat. Nos. 6,118,049; 4,876,197; and 4,880,734; herein incorporated by reference). The activity of chimeric promoters can be assayed using any suitable assay, including, but not limited to, those disclosed herein.

II. Regulation of Gene Expression

A. dsRNA

In some embodiments, the novel bi-directional promoters of the present invention are used to produce dsRNA for the regulation of gene expression (e.g., in plants). The role of dsRNA in regulation of gene expression and virus resistance has only recently been elucidated. A variety of organisms have been shown to exhibit a decrease in gene expression in response to foreign nucleic acids homologous to the gene being regulated. In one category, termed post-transcriptional gene silencing (PTGS), transcription of the target locus in unaffected, but the half-life of the RNA decreases dramatically (Fire, Trends In Genetics, 15:358 [1999]).

A variety of PTGS phenomenon, including cosuppression (plants), virus resistance in plants, quelling (*Neurospora crassa*), and RNA interference (gene silencing in Drosophila and *C. elegans*) can all be attributed to regulation by dsRNA (See e.g., Marx, Science, 288:1370 [2000]; Montgomery and Fire, Trends in Genetics, 14:255 [1998]; Ngo et al, PNAS, 95:14687 [1998]). All of these effects can be attributed to the regulation of gene expression through the degradation of mRNA.

The present invention is not limited to any one mechanism. Indeed, an understanding of the mechanism is not required to practice the present invention. Nonetheless, it is contemplated that gene regulation via dsRNA involves a ribonuclease. Genetic experiments indicate that one of the genes required for gene silencing is a ribonuclease. In addition, biochemical experiments indicate that dsRNAs involved in gene regulation are broken down into short pieces. The mRNA of the gene being regulated is broken down into similar sized pieces. It is contemplated that the dsRNA then interacts with a specific ribonuclease which it targets to the mRNA of interest (Hammond et el., Nature, 404:293 [2000]). It is further contemplated that plants and other organisms use dsRNA-mediated degradation as a defense against viral infections. The defense takes advantage of the fact that many viruses produce dsRNA as an intermediate. The host organism then utilizes the dsRNA to degrade viral mRNAs essential for replication and spreading.

It is further contemplated that dsRNA is used to regulate the spread of transposable elements, preventing extensive transposition events that may cause harmful mutations (Marx, Science, 288:1370 [2000]). It is also contemplated that dsRNA-mediated gene regulation is involved in embryo development. It has been demonstrated that dsRNA can spread throughout plants and *C. elegans*, and can be spread to first generation progeny (Fire et al., Nature, 391:8–6 [1998]; Palauqui et al., EMBO J., 16:4738 [1997]; Voinnet and Baulcombe, Nature, 389:553 [1997]).

B. Genes

In some embodiments, the compositions and methods of the present invention are used to regulate gene expression. The methods are not limited to the regulation of any particular gene. Indeed, a variety of genes are contemplated for regulation, including, but not limited to those, described below.

In some embodiments, the gene regulated is an endogenous plant gene. The methods of the present invention are not limited to any particular plant. Indeed, a variety of plants are contemplated, including, but not limited to angiosperms, gymnosperms, monocotyledons, and dicotyledons. Specific plants contemplated include, but are not limited to, wheat, barley, maize, rye, rice, soybean, hemp, triticale, apricots, oranges, quince, melon, plum, cherry, peach, nectarine, strawberry, grape, raspberry, blackberry, pineapple, papaya, mango, banana, grapefruits, apples, pears, avocados, walnuts, almonds, filberts, pecans, carrots, lettuce, zucchini, tomatoes, beans, peas, cabbage, chicory, onion, garlic, pepper, squash, pumpkin, celery, turnips, radish, spinach, cauliflower, potatoes, sweet potatoes, broccoli, eggplant, cucumber, asparagus, poplar, pine, sequoia, cedar, oak, tobacco, clover, lotus, jojoba, rapeseed, sunflower, sorghum, sugarcane, sugar beet, safflower, arabidopsis, alfalfa, and cotton.

In some embodiments, the compositions and methods of the present invention are used to regulate the expression of a gene involved in a metabolic pathway of a plant cell (e.g., genes responsible for the synthesis or metabolism of peptides, proteins, fatty acids, lipids, waxes, oils, starches, sugars, carbohydrates, flavors, odors, fragrances, toxins, carotenoid pigments, hormones, cell wall polymers, gene regulatory molecules, flavonoids, storage proteins, phenolic acids, coumarins, alkaloids, quinones, lignins, glucosinolates, tannins, aliphatic amines, celluloses, polysaccharides, glycoproteins and glycolipids), in resistance or susceptibility of a plant to diseases (e.g., to viral infection), in a visible phenotype (e.g., flower color intensity, color hue and color pattern); or cell differentiation. For example, specific genes contemplated include, but are not limited to, those described in U.S. Pat. Nos. 5,107,065; 5,283,184; and 5,034,323; each of which is herein incorporated by reference.

In other embodiments, the compositions and methods of the present invention are used to alter the expression of a plant gene whose function is unknown in order to elucidate its function. Sense and antisense fragments of the gene are introduced to the plant. The plant is then examined for phenotypic changes (e.g., metabolic or visible).

In yet other embodiments, the compositions and methods of the present invention are used to alter the expression of a gene of any additional organisms, including, but not limited to, a prokaryotic, eukaryotic, or fungal gene. The gene may be involved in a metabolic pathway, in resistance or susceptibility to a disease, in a visible phenotype, in cell differentiation, or may be a gene of unknown function.

C. Methods of Producing dsRNA

In some embodiments of the present invention, the LjPLP-IV promoter (e.g., SEQ ID NO:4) is used to regulate gene expression in an organism (e.g., a plant). Bi-directional promoters are known to regulate production of mRNA in opposite directions from the same promoter (See e.g., Arakawa et al., Transgenic Research 6:403 [1997]; Keddie et al, Plant Mol. biol., 24:327 [1994]; Leung et al., Mol. Gen. Genet., 230:463 [1991]; U.S. Pat. Nos. 5,952,195 and 5,646, 012, each of which is herein incorporated by reference).

Methods are known for the production of dsRNA in plants (See e.g., Waterhouse et al., PNAS, 95:13959 [1998]; and PCT Publication WO 99/61631, which is herein incorporated by reference). Many of the methods previously described express the sense and antisense transcripts from separate promoters or in tandem as one piece of RNA to produce dsRNA. The present invention utilizes bi-directional promoters to produce both the sense and antisense transcripts from the same promoter construct, thus simplifying the construction of expression vectors and eliminating the need for recombination steps. Suitable constructs for the transformation of plants and animals are well known in the art, including but not limited to those described below.

D. Methods of Transforming Plants

1. Vectors

Gene sequences intended for expression in plants are first assembled in expression cassettes comprising a promoter (e.g., the LjPLP-IV promoter of SEQ ID NO:4). Methods which are well known to those skilled in the art may be used to construct expression vectors containing nucleic acid sequences of interest and appropriate transcriptional and translational control elements. These methods include in vitro recombinant DNA techniques, synthetic techniques, and in vivo genetic recombination. Such techniques are widely described in the art (See e.g., Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y, both of which are herein incorporated by reference).

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (See e.g., Odell et al., Nature 313:810 [1985]; Rosenberg et al., Gene, 56:125 [1987]; Guerineau et al., Mol. Gen. Genet., 262:141 [1991]; Proudfoot, Cell, 64:671 [1991]; Sanfacon et al., Genes Dev., 5:141; Mogen et al., Plant Cell, 2:1261 [1990]; Munroe et al., Gene, 91:151 [1990]; Ballas et al., Nucleic Acids Res. 17:7891 [1989]; Joshi et al., Nucleic Acid Res., 15:9627 [1987]).

In addition, in some embodiments, constructs for expression of the gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Callis et al., Genes Develop. 1: 1183 [1987]). Intron sequences have been routinely incorporated into plant transformation vectors, typically within the non-translated leader.

In some embodiments of the present invention, the construct for expression of the nucleic acid sequence of interest also includes a regulator such as a nuclear localization signal (Kalderon et al., Cell 39:499 [1984]; Lassner et al., Plant Molecular Biology 17:229 [1991]), a plant translational consensus sequence (Joshi, Nucleic Acids Research 15:6643 [1987]), an intron (Luehrsen and Walbot, Mol.Gen. Genet. 225:81 [1991]), and the like, operably linked to the nucleic acid sequence of interest.

In preparing the construct comprising the nucleic acid sequence of interest, various DNA fragments can be manipulated, so as to provide for the DNA sequences in the desired orientation (e.g., sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (e.g., transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra, Gene 19: 259 [1982]; Bevan et al., Nature 304:184 [1983]), the bar gene which confers resistance to the herbicide phosphinothricin (White et al., Nucl Acids Res. 18:1062 [1990]; Spencer et al., Theor. Appl. Genet. 79: 625 [1990]), the hph gene which confers resistance to the antibiotic hygromycin (Blochlinger and Diggelmann, Mol. Cell. Biol. 4:2929 [1984]), and the dhfr gene, which confers resistance to methotrexate (Bourouis et al., EMBO J., 2:1099 [1983]).

In some embodiments of the present invention, transformation is carried out using *Agrobacterium tumefaciens* mediated methods. Many vectors are available for transformation using *Agrobacterium tumefaciens*. These typically carry at least one T-DNA border sequence and include vectors such as pBIN19 (Bevan, Nucl. Acids Res., 12:8711 [1984]). An additional vector useful for Agrobacterium-mediated transformation is the binary vector pCIB 10 (Rothstein et al., Gene 53:153 [1987]) which contains a gene encoding kanamycin resistance for selection in plants, T-DNA right and left border sequences and incorporates sequences from the wide host-range plasmid pRK252 allowing it to replicate in both *E. coli* and Agrobacterium. Various derivatives of pCIB10 have been constructed which incorporate the gene for hygromycin B phosphotransferase (See e.g., Gritz et al., Gene, 25: 179 [1983]). These derivatives enable selection of transgenic plant cells on hygromycin only (pCIB743), or hygromycin and kanamycin (pCIB715, pCIB717).

In some embodiments of the present invention, where the nucleic acid sequence of interest is introduced directly into a plant. One vector useful for direct gene transfer techniques in combination with selection by the herbicide Basta (or phosphinothricin) is a modified version of the plasmid pCIB246, with the CaMV 35S promoter replaced by a promoter of the present invention (e.g., SEQ ID NO:4) in operational fusion to the *E. coli* GUS gene and the CaMV 35S transcriptional terminator and is described in WO 93/07278, which is herein incorporated by reference. In some embodiments of the present invention, this vector is modified to include a promoter of the present invention (e.g., SEQ ID NO:4) operatively linked to two nucleic acid sequences of interest. The gene providing resistance to phosphinothricin is the bar gene from *Streptomyces hygroscopicus* (Thompson et al., EMBO J., 6:2519 [1987]).

2. Transformation Techniques

Once the nucleic acid sequences have been operatively linked to a promoter of the present invention and inserted into a suitable vector for the particular transformation technique utilized (e.g., one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, direct transformation in the plastid genome is used to introduce the vector into the plant cell (See e.g., U.S. Pat. Nos. 5,451,513; 5,545,817; 5,545,818; PCT application WO 95/16783; all of which are herein incorporated by reference). The basic technique for chloroplast transformation involves introducing regions of cloned plastid DNA flanking a selectable marker together with the nucleic acid encoding the RNA sequences of interest into a suitable target tissue (e.g., using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al., PNAS, 87:8526 [1990]; Staub and Maliga, Plant Cell, 4:39 [1992]). The presence of cloning sites between these markers allowed creation of a plastid targeting vector introduction of foreign DNA molecules (Staub and Maliga, EMBO J., 12:601 [1993]). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga, PNAS, 90:913 [1993]). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway, Mol. Gen. Genet, 202:179 [1985]). In still other embodiments, the vector is transferred into the plant cell by using polyethylene glycol (Krens et al, Nature, 296:72 [1982]; Crossway et al., BioTechniques, 4:320 [1986]); fusion of protoplasts with other entities, either minicells, cells, lysosomes or other fusible lipid-surfaced bodies (Fraley et al., Proc. Natl. Acad. Sci., USA, 79:1859 [1982]); protoplast transformation (EP 0 292 435; herein incorporated by reference); direct gene transfer (Paszkowski et al., EMBO J., 3:2717 [1984]; Hayashimoto et al., Plant Physiol. 93:857 [1990]).

In still further embodiments, the vector may also be introduced into the plant cells by electroporation. (Fromm, et al., Pro. Natl Acad. Sci. USA 82:5824, 1985; Riggs et al, Proc. Natl. Acad. Sci. USA 83:5602 [1986]). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, the vector is introduced through ballistic particle acceleration using devices (e.g., available from Agracetus, Inc., Madison, Wis. and Dupont, Inc., Wilmington, Del). (See e.g., U.S. Pat. No. 4,945,050; herein incorporated by reference; and McCabe et al., Biotechnology 6:923 [1988]). See also, Weissinger et al., Annual Rev. Genet. 22:421 [1988]; Sanford et al., Particulate Science and Technology, 5:27 [1987] (onion); Svab et al., Proc. Natl. Acad. Sci. USA, 87:8526 [1990] (tobacco chloroplast); Christou et al., Plant Physiol., 87:671 [1988] (soybean); McCabe et al., Bio/Technology 6:923 [1988] (soybean); Klein et al., Proc. Natl. Acad. Sci. USA, 85:4305 [1988] (maize); Klein et aL, Bio/Technology, 6:559 [1988] (maize); Klein et al., Plant Physiol., 91:4404 [1988] (maize); Fromm et al., Bio/Technology, 8:833 [1990]; and Gordon-Kamm et al., Plant Cell, 2:603 [1990] (maize); Koziel et al., Biotechnology, 11:194 [1993] (maize); Hill et al., Euphytica, 85:119 [1995] and Koziel et al., Annals of the New York Academy of Sciences 792:164 [1996]; Shimamoto et al., Nature 338: 274 [1989] (rice); Christou et aL, Biotechnology, 9:957 [1991] (rice); Datta et al., Bio/Technology 8:736 [1990] (rice); European Patent Application EP 0 332 581, herein incorporated by reference (orchardgrass and other Pooideae); Vasil et al., Biotechnology, 11: 1553 [1993] (wheat); Weeks et al., Plant Physiol., 102: 1077 [1993] (wheat); Wan et al., Plant Physiol. 104: 37 [1994] (barley); Knudsen and Muller, Planta, 185:330 [1991] (barley); Umbeck et al., Bio/Technology 5: 263 [1987] (cotton); Casas et al., Proc. Natl. Acad. Sci. USA 90:11212 [1993] (sorghum); Somers et al., Bio/Technology 10:1589 [1992] (oat); Torbert et al., Plant Cell Reports, 14:635 [1995] (oat); Weeks et al., Plant Physiol., 102:1077 [1993] (wheat); and Chang et al., WO 94/13822 (wheat).

In addition to direct transformation, in some embodiments, the vectors comprising the nucleic acid sequences of interest and a promoter of the present invention are transferred using Agrobacterium-mediated transformation (Hinchee et al., Biotechnology, 6:915 [1988]; Ishida et al., Nature Biotechnology 14:745 [1996]). Agrobacterium is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (e.g., nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell, Science, 237: 1176 [1987]). Species which are susceptible infection by Agrobacterium may be transformed in vitro.

3. Regeneration

After determination of the presence and expression of the desired gene products, whole plants are regenerated. Plant regeneration from cultured protoplasts is described in Evans et al., Handbook of Plant Cell Cultures, Vol. 1: (MacMillan Publishing Co. New York, 1983); and Vasil I. R. (ed.), Cell Culture and Somatic Cell Genetics of Plants, Acad. Press, Orlando, Vol. 1, 1984, and Vol. III, 1986. It is known that many plants can be regenerated from cultured cells or tissues, including but not limited to all major species of sugarcane, sugar beet, cotton, fruit and other trees, legumes and vegetables, and monocots (e.g., the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

E. Regulation of Gene Expression in Other Organisms

The compositions and methods of the present invention are not limited to the regulation of gene expression in plants. It is contemplated that the compositions and methods of the present invention may be utilized in the regulation of gene expression in a variety of organisms, including, but not limited to, Drosophila (See e.g., Kennerdell and Carthew, Cell, 95:1017 [1998]; Misquitta and Paterson, PNAS, 96:1451 [1999]), *C. elegans* (See e.g., Fire et al., Nature, 391:806 [1998]), *Trypanosoma brucei* (See e.g., Ngo et al., PNAS, 95:14687 [1998]), Paramecium (See e.g., Ruiz et al., Mol. Cell. Biol., 9:931 [1998]), mammalian cells (See e.g., Bahramian and Zarbl, Mol. Cell. Bio., 19:274 [1999]), Hydra (See e.g., Lohmann et al., Dev. Biol., 214:211 [1999]), and *Neurospora crassa* (Romano and Macino, Mol. Microbiol., 6:3343 1992]).

Methods of introducing foreign nucleic acids (e.g., DNAs coding for sense and antisense versions of a gene under the control of a promoter of the present invention) are known in the art (See e.g., for paramecium (Ruiz etal., Mol. Cell. Biol., 9:931 [1998]; Bourgain and Katinka, Nuc. Acid. Res., 19:1541 [1991]); Trypanosoma (Ngo et al., PNAS, 95:14687 [1998]); rodent fibroblasts (Bahramian and Zarbl, Mol. Cell. Bio., 19:274 [1999]); and Drosophila (Misquitta and Paterson, PNAS, 96:1451 [1999]; Hidalgo et al., Development, 121:3703 [1995]; Hidalgo and Brand, Development, 124: 3253 [1997]). In some embodiments, the promoter utilized for regulation of gene expression comprises a chimeric construct that provides additional regulatory sequences for expression in a given organism. Suitable elements are known in the art (e.g., including, but not limited to, those described herein).

III. Methods of Production of Recombinant Proteins

In some embodiments, the present invention provides methods of producing one or more proteins of interest using a LjPLP-IV promoter of the present invention. In some embodiments, the bi-directional LjPLP-IV promoter (e.g., SEQ ID NO:4) is used to express two proteins of interest (e.g., two subunits of a multi-subunit protein or two members of a metabolic pathway) from the same promoter construct. In other embodiments, a sequence that hybrizides to SEQ ID NO:4 is utilized. In yet other embodiments, a sequence containing a portion of SEQ ID NO:4 is utilized (e.g., a chimeric promoter). One skilled in the art will recognize, in view of the present disclosure, that the expression vectors comprising a promoter of the present invention and nucleic acid sequences encoding one or more polypeptides may contain additional regulatory and enhancer elements specific to the host cell utilized for expression (e.g., those described above or below).

In some embodiments, one or more proteins of interest are expressed in regenerated plants (e.g., in a specific tissue to elicit a specific metabolic response). In other embodiments, polypeptides of interest are expressed in plants for use in food stuffs (e.g., to increase the nutritional value or to express a pharmaceutical compound). In still further embodiments, one or more polypeptides of interest are expressed in cell culture (e.g., plant, bacterial, or eukaryotic cells) for the purpose of purifying the polypeptides of interest from the cell culture.

A variety of expression vector/host systems may be utilized to contain and express sequences encoding a polypeptide of interest. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV); tobacco mosaic virus (TMV); brome mosaic virus) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements may be utilized. For example, when cloning in bacterial systems, in addition to a promoter of the present invention, inducible elements such as those included in the hybrid lacZ promoter of the BLUESCRIPT phagemid (Stratagene, LaJolla, Calif.) or PSPORT1 plasmid (Life Technologies, Inc., Rockville, MD) and the like may be used. For expression in insect cells, the promoter may comprise elements of the baculovirus polyhedrin promoter. For expression mediated by plant viruses, viral promoters or leader sequences may be included in the vector. In mammalian expression systems, elements from mammalian genes or from mammalian virus promoters may be included.

In some preferred embodiments, the 5' leader sequence is included in the expression cassette construct. Such leader sequences can act to enhance translation. Translation leaders are known in the art and include: picornavirus leaders, for example, EMCV leader (Encephalomyocarditis 5' non-coding region; Elroy-Stein et al., PNAS, 86:6126 [1989]); potyvirus leaders, for example, TEV leader (Tobacco Etch Virus; Niepel and Gallie, J Virol., 73:9080 [1999]) MDMV leader (Maize Dwarf Mosaic Virus; Virology, 154:9 [1986]), and human immunoglobulin heavy-chain binding protein (BiP; Macejak and Samow, Nature 353:90 [1991]); untranslated leader from the coat protein mRNA of alfalfa mosaic virus (AMV RNA 4; Jobling and Gebrke, Nature, 325:622 [1987]); tobacco mosaic virus leader (TMV; Gallie et al., Molecular-Biology of RNA, pages 237–256 [1989]); and maize chlorotic mottle virus leader (MCMV; Lommel et al., Virology 91:382 [1991]; Della-Cioppa et al., Plant Physiology 84:965 [1987]).

A. Bacterial Expression

In some embodiments, one or more polypeptides of interest are expressed in bacterial expression systems. A number of suitable expression vectors may be modified to include a promoter of the present invention. The selection of vector depends upon the use intended for the polypeptide of interest. For example, when large quantities of the polypeptide are needed for the induction of antibodies, vectors which direct high level expression of fusion proteins that are readily purified may be used. Such vectors include, but are not limited to, the multifunctional *E. coli* cloning and expression vectors such as BLUESCRIPT® phagemid (Stratagene, La Jolla, Calif.), in which the sequence encoding the polypeptide of interest may be ligated into the vector in frame with sequences for the amino-terminal Met and the subsequent 7 residues of beta-galactosidase so that a hybrid protein is produced; pIN vectors (Van Heeke and Schuster, J. Biol. Chem., 264:5503 [1989]; and the like. pGEMX vectors (Promega Corporation, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

B. Yeast Expression

In some embodiments of the present invention, one or more proteins of interest are expressed in yeast (e.g., *Saccharomyces cerevisiae*). In these embodiments, the vectors utilized may contain, in addition to a promoter of the present invention (e.g., SEQ ID NO:4), promoter elements from constitutive or inducible promoters such as alpha factor, alcohol oxidase, and PGK are used. For reviews, See e.g., Ausubel et al. (supra) and Grant et al., Methods Enzymol., 153:516 [1987].

C. Plant Expression

In some embodiments, proteins are expressed in a plant. In some embodiments, the methods described above are utilized for expression in plants. In some embodiments, expression is directed to a specific tissue of the plant by including additional tissue-specific regulatory elements in the promoter construct (e.g., those described above).

In some embodiments, one or more polypeptides of interest are expressed in plants using Agrobacterium-mediated transformation (See Example 2 for an illustrative example). Chimeric gene constructs are prepared using standard molecular biological techniques. A LjPLP promoter (e.g., SEQ ID NO:4) is cloned into the unique BamHI restriction site of the pB1101 (Clonetech) derived binary vector. Genes encoding the polypeptides of interest are cloned into the vector in both forward and reverse orientation relative to the promoter.

The vectors are then transferred into *Agrobacterium rhizogenes* A4 (Tempe and Casse-Delbart, in Schell and Vasil (eds), Cell Culture and Somatic Cell Genetics of Plants, Vol. 6. Academic Press, San Diego, Calif., pp. 25–49 [1989]) by using the freeze-thaw method of Hofgen and Willmitzer (Nuc. Acid. Res., 16:9877 [1988]). Transgenic *Lotus corniculatus* cv. Rodeo plants are generated as previously described (Szabados et al., Plant Cell, 2:973 [1990]; Szczyglowski et al., Plant Cell, 6:317 [1994]).

In other embodiments, plant vectors are created using a recombinant plant virus containing a recombinant plant viral nucleic acid, as described in PCT publication WO 96/40867 which is herein incorporated by reference. Subsequently, the recombinant plant viral nucleic acid which contains one or more nucleic acid sequences encoding polypeptides of interest are transcribed or expressed in the infected tissues of the plant host and the polypeptides are recovered from the plant, as described in WO 99/36516, which is herein incorporated by reference.

In this embodiment, recombinant plant viral nucleic acids which contain a promoter of the present invention linked to two nucleic acid sequences encoding one or more polypeptides of interest are utilized. The recombinant plant viral nucleic acids have substantial sequence homology to plant viral nucleotide sequences and may be derived from an RNA, DNA, cDNA or a chemically synthesized RNA or DNA. A partial listing of suitable viruses is described below.

The first step in producing recombinant plant viral nucleic acids according to this particular embodiment is to modify the nucleotide sequences of the plant viral nucleotide sequence by known techniques such that a promoter of the present invention (e.g., SEQ ID NO:4) is inserted into the plant viral nucleic acid without destroying the biological function of the plant viral nucleic acid. The native coat protein coding sequence may be deleted in some embodiments, placed under the control of a non-native subgenomic promoter in other embodiments, or retained in a further embodiment. If it is deleted or otherwise inactivated, a non-native coat protein gene is inserted under control of one of the non-native subgenomic promoters, or optionally under control of the native coat protein gene subgenomic promoter. The non-native coat protein is capable of encapsidating the recombinant plant viral nucleic acid to produce a recombinant plant virus. Thus, the recombinant plant viral nucleic acid contains a coat protein coding sequence, which may be native or a nonnative coat protein coding sequence, under control of one of the native or non-native subgenomic promoters. The coat protein is involved in the systemic infection of the plant host.

Some of the viruses suitable for use in the present invention include, but are not limited to viruses from the tobamovirus group such as Tobacco Mosaic virus (TMV), Ribgrass Mosaic Virus (RGM), Cowpea Mosaic virus (CMV), Alfalfa Mosaic virus (AMV), Cucumber Green Mottle Mosaic virus watermelon strain (CGMMV-W) and Oat Mosaic virus (OMV) and viruses from the brome mosaic virus group such as Brome Mosaic virus (BMV), broad bean mottle virus and cowpea chlorotic mottle virus. Additional suitable viruses include Rice Necrosis virus (RNV), and geminiviruses such as tomato golden mosaic virus (TGMV), Cassava latent virus (CLV) and maize streak virus (MSV).

Other embodiments of plant vectors used for the expression of sequences encoding polypeptides include, for example, a promoter of the present invention used in combination with the omega leader sequence from TMV (Takamatsu, EMBO J. 6:307 [1987]). These constructs can be introduced into plant cells by any suitable methods, including, but not limited to those described above.

D. Expression in Insect Cells

In still further embodiments, an insect system is used to express one or more polypeptides of interest. For example, in one such system, *Autographa californica* nuclear polyhedrosis virus (AcNPV) is used as a vector to express foreign genes in *Spodoptera frugiperda* cells or in Trichoplusia larvae. The sequences encoding polypeptides of interest may be cloned into a non-essential region of the virus, such as the polyhedrin gene, and placed under control of the a promoter of the present invention that additionally comprises elements of a polyhedrin promoter. Successful insertion of the nucleic acid sequence encoding the polypeptide of interest will render the polyhedrin gene inactive and produce recombinant virus lacking coat protein. The recombinant viruses may then be used to infect, for example, *S. frugiperda* cells or Trichoplusia larvae in which the polypeptide may be expressed (Engelhard et al, Proc. Nat. Acad. Sci. 91:3224 [1994]).

E. Expression in Mammalian Cells

In yet other embodiments, a mammalian cell expression system is utilized to express one or more polypeptides of interest. In mammalian host cells, a number of viral-based expression systems may be utilized. In cases where an adenovirus is used as an expression vector, sequences encoding polypeptides may be ligated into an adenovirus transcription/translation complex consisting of a promoter of the present invention (e.g., SEQ ID NO:4) and elements of a late promoter and tripartite leader sequence. Insertion in a non-essential E1 or E3 region of the viral genome may be used to obtain a viable virus which is capable of expressing one or more polypeptides of interest in infected host cells (Logan and Shenk, Proc. Natl. Acad. Sci., 81:3655 [1984]). In addition, transcription enhancers, such as the Rous sarcoma virus (RSV) enhancer, may be used to increase expression in mammalian host cells.

Specific initiation signals may also be used to achieve more efficient translation of sequences encoding one or more polypeptides of interest. Such signals include the ATG initiation codon and adjacent sequences. In cases where sequences encoding the polypeptides of interest, their initiation codons, and upstream sequences are inserted into the appropriate expression vector, no additional transcriptional or translational control signals may be needed. However, in cases where only coding sequence, or a portion thereof, is inserted, exogenous translational control signals including the ATG initiation codon are provided. Furthermore, the initiation codon is provided in the correct reading frame to ensure translation of the entire insert containing one or more polypeptides of interest. Exogenous translational elements and initiation codons may be of various origins, both natural and synthetic. The efficiency of expression may be enhanced by the inclusion of enhancers which are appropriate for the particular cell system which is used, such as those described in the literature (Scharf et al., Results Probl. Cell Differ., 20:125 [1994]).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express one or more polypeptides of interest may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells that successfully express the polypeptides of interest. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., Cell 11:223 [1977]) and adenine phosphoribosyltransferase (Lowy et al., Cell 22:817 [1980]) genes that can be employed in tk⁻ or aprt⁻ cells, respectively. Also, antimetabolite, antibiotic, or herbicide resistance can be used as the basis for selection; for example, dhfr, which confers resistance to methotrexate (Wigler et al., Proc. Natl. Acad. Sci., 77:3567 [1980]); npt, which confers resistance to the aminoglycosides neomycin and G-418 (Colbere-Garapin et al., J. Mol. Biol., 150:1 [1981]); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman. and Mulligan, Proc. Natl. Acad. Sci., 85:8047 [1988]). In some embodiments, visible markers such as anthocyanins, β-glucuronidase and its substrate GUS, GFP, and luciferase and its substrate luciferin, are utilized to identify transformants and to quantify the amount of transient or stable protein expression attributable to a specific vector system (Rhodes et al., Methods Mol. Biol., 55:121 [1995]).

F. Confirmation of Protein Expression

Although the presence/absence of marker gene expression suggests that the gene of interest is also present, its presence and expression may need to be confirmed. For example, if the sequence encoding the polypeptide(s) of interest is inserted within a marker gene sequence, recombinant cells containing sequences encoding the polypeptide can be identified by the absence of marker gene function. Alternatively, a marker gene can be placed in tandem with a sequence encoding one of the polypeptides of interest under the control of the same promoter of the present invention (e.g., SEQ ID NO:4). Expression of the marker gene in response to induction or selection usually indicates expression of the tandem gene as well.

Alternatively, host cells that contain the nucleic acid sequence encoding the polypeptide of interest and express the polypeptide may be identified by a variety of procedures known to those of skill in the art. These procedures include, but are not limited to, DNA-DNA or DNA-RNA hybridizations and protein bioassay or immunoassay techniques, which include membrane, solution, or chip, based technologies for the detection and/or quantification of nucleic acid or protein.

The presence of polynucleotide sequences encoding a polypeptide of interest can be detected by DNA-DNA or DNA-RNA hybridization or amplification using probes or portions or fragments of polynucleotides encoding the polypeptide. Nucleic acid amplification based assays involve the use of oligonucleotides or oligomers based on the sequences encoding the polypeptide to detect transformants containing DNA or RNA encoding the polypeptide.

A variety of protocols for detecting and measuring the expression of a polypeptide using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on the polypeptide is preferred, but a competitive binding assay may be employed. These and other assays are described, among other places, in Hampton et al., 1990; Serological Methods, a Laboratory Manual, APS Press, St Paul, Minn.; and Maddox et al., J. Exp. Med., 158:1211 [1983]).

A wide variety of labels and conjugation techniques are known by those skilled in the art and may be used in various nucleic acid and amino acid assays. Means for producing labeled hybridization or PCR probes for detecting sequences related to polynucleotides encoding a polypeptide of interest include oligonucleotide labeling, nick translation, end-labeling or PCR amplification using a labeled nucleotide. Alternatively, the sequences encoding the polypeptide, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits from Pharmacia & Upjohn (Kalamazoo, Mich.), Promega Corporation (Madison, Wis.) and U.S. Biochemical Corp. (Cleveland, Ohio). Suitable reporter molecules or labels, which may be used, include radionucleotides, enzymes, fluorescent, chemiluminescent, or chromogenic agents as well as substrates, cofactors, inhibitors, magnetic particles, and the like.

G. Recovery of Expressed Proteins

In some embodiments of the present invention, it is desirable to recover expressed proteins from cell culture. Host cells transformed with nucleotide sequences encoding one or more polypeptides of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides that encode the polypeptide(s) of interest may be designed to contain signal sequences that direct secretion of the polypeptide through a prokaryotic or eukaryotic cell membrane. Other recombinant constructions may be used to join sequences encoding the polypeptide to nucleotide sequence encoding a polypeptide domain that will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (available from Invitrogen, San Diego, Calif.) between the purification domain and the polypeptide of interest may be used to facilitate purification. One such expression vector provides for expression of a fusion protein containing the polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath et al, Prot. Exp. Purif., 3:263 [1992] while the enterokinase cleavage site provides a means for purifying the polypeptide from the fusion protein. A discussion of vectors which contain fusion proteins is provided in Kroll et al, DNA Cell Biol., 12:441 [1993]).

Experimental

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); µmol (nanomoles); g (grams); mg (milligrams); µg (micrograms); ng (nanograms); l or L (liters); ml (milliliters); µl (microliters); cm (centimeters); mm (millimeters); µm (micrometers); nm (nanometers); C (degrees Centigrade); U (units), mU (milliunits); min. (minutes); sec. (seconds); % (percent); kb (kilobase); bp (base pair); cDNA (copy or complimentary DNA); PCR (polymerase chain reaction); RT-PCR (reverse-transcriptase PCR); BSA (bovine serum albumin); SDS (sodium dodecyl sulfate); Tris (tris(hydroxymethyl)-aminomethane); Sigma (Sigma Chemical Co., St. Louis, Mo.); Boehringer Mannheim (Boehringer Mannheim, Corp., Indianapolis, Ind.); Stratagene (Stratagene Inc., La Jolla, Calif.); Pierce (Pierce, Rockford, Ill.); and NEB (New England Biolabs, Beverly, Mass.).

EXAMPLE 1

Identification and Cloning of L. japonicus PLP-IV Promoter Nucleic Acid

A. Plant Material and Growth Conditions

L. japonicus ecotype B-129-S9 Gifu plants were germinated and grown as described previously (Kapranov et al., Plant Physiol., 113:1081 [1997]; Szczyglowski et al., Plant Physiol., 114:1335 [1997]). Nodules, leaves, and stems of L. japonicus plants inoculated with Mezorhizobium loti strain NZP2235 (Jarvis et al., Int. J. Syst. Bact., 32:378 [1982]) were harvested 35 days after inoculation. Control uninoculated roots were collected from axenically grown L. japonicus plants of the same age. L. japonicus flowers were obtained from 2 to 3 month old plants.

Transgenic Lotus corniculatus plants were inoculated with M. loti strain 2037 (Pankhurst et al., J. Gen. Microbiol., 132:2321 [1986]) and subsequently grown in a 6:1 mixture of vermiculite and sand under controlled environmental conditions (18-/6-h day/night cycle; 250 µE s-i m-2 22/18C day/night temperature). B&D solution (Broughton and Dilworth, Biochem. J., 124:1075 [1971]), supplemented with 1 mM KNO3, was used to water these plants. Fully mature nodules, leaves, and root segments were harvested from transgenic plants 42–45 day, and used directly for histochemical analysis.

B. Screening of L. japonicus Genomic DNA and Nodule-Specific cDNA Libraries

A L. japonicus genomic DNA library, and a cDNA library from mature nodules of the same plant species were provided by J. Stougaard (Aarhus University, Denmark). The genomic library was constructed in the FIX II λ vector (Stratagene) and the cDNA library was constructed with oligo (dT) primers in the λ-UniZAP vector (Stratagene). Filters carrying the libraries were pre-hybridized and hybridized in a buffer containing 0.5 M sodium phosphate, pH 7.2, 7% SDS, and 1% BSA, at 65° C. The filters were washed at either low-stringency (last wash in 2× SSC, 0.1% SDS at 65° C. for 15 minutes), or high stringency (last wash in 0.1× SSC, 0.1% SDS at 65° C. for 15 minutes) conditions, as specified.

To isolate LjPLP-IV cDNA, the L. japonicus cDNA Library was screened with the PIPT-like domain-containing fragment of the LjPLP-IcDNA (base pairs 44–1282) under low-stringency conditions.

C. Nucleic Acid Isolation and Northern Analysis

Genomic DNA and total RNA from various L. japonicus tissues were isolated as described by Kapranov et al., Plant Physiol., 113:1081 [1997]; Szczyglowski et al., Plant Physiol., 114:1335 [1997]. Northern blot analyses were performed essentially as described (Kapranov et al., Plant Physiol., 113:1081 [1997]; Szczyglowski et al., Plant Physiol., 114:1335 [1997]). For hybridization with strand-specific RNA probes, the filters were pre-hybridized in 100 mM potassium phosphate buffer, pH 6.8, 5× SSC, 1× Denhardts, 0.1% SDS, 100 µg/ml denatured salmon sperm DNA, at 50° C. for 4 hours. Hybridization was carried out in 70 mM potassium phosphate buffer, pH 6.8, 3.6× SSC, 0.7× Denhardt's, 7.0% dextran sulphate, 71 µg/ml denatured salmon sperm DNA, and 50% deionized formamide, at 65° C. The filters were washed for 15 minutes in 2× SSC, 0.1% SDS; 15 minutes in 1× SSC, 0.1%SDS; and 15 minutes in 0.1× SSC, 0.1% SDS, at 65° C.

Radiolabeled RNA probes were prepared as follows: Template DNA (0.5–1 µg) was linearized and incubated in a buffer containing 40 mM Tris, pH 7.5, 8mM $MgCl_2$, 2 mM spermidine, 25 mM NaCl, 10 mM DTT, 40 units placental RNAse inhibitor (BMB), 0.5 mM ATP, 0.5 mM GTP, 0.5 mM CTP, 0.5 µM UTP, 50 µCi [α-32P]UTP, and 20 units of T3 or T7 RNA polymerase (BMB), in a total volume of 20 µl. The labeling reactions were performed for 1 hr at 37° C. The DNA template was removed from the reaction mix by adding 10 units of RNAse-free DNAse I (BMB) and incubated at 37° C. for 15 minutes. Radiolabeled RNA probes were purified on Bio-Spin 6 chromatography Columns (Bio-Rad).

D. RT-PCR

RT-PCR was used to clone the LjPLP-IV mRNA. Total RNA (5 µg) from lotus nodules and flowers was denatured for 10 min at 65° C., and reverse transcribed for 1 hour at 42° C., in a reaction mix containing 50 mM Tris-HCl pH 8.3, 75 mM KCl, 3 mM $MgCl_2$, 10 mM DTT, 1 mM of each dNTP, 40 units of placental RNAse inhibitor (BMB), 100 ng of DB544 primer (5'-CAAGCAATTTGCTTTGATAC-3'; SEQ ID NO: 1), and 200 units of Superscript II reverse transcriptase (Gibco) in a total volume of 25 µl.

A subsequent PCR amplification step was performed using 4 µl of the original cDNA reaction mix and 40 ng of forward and reverse primers in a total volume of 25 μl. The forward N16-5'-4 (5'-GGGAGTGCTTTTGTTCTCTGC; SEQ ID NO:2) primer was designed based on the nucleotide sequence of genomic region 77 bp upstream from the putative ATG codon of the LjPLP-IV protein. The reverse DB641 primer (5'-CTTGTCACATAAGCAAAAGG; SEQ ID NO:3) was designed to be complementary to the nucleotide sequence of the 3'UTR of LjNOD16 cDNA. Two consecutive rounds of PCR amplification were performed. The 1.9 kb PCR product was cloned into the yeast YePlac195PGK expression vector and its nucleotide sequence was determined.

EXAMPLE 2

Generation of Transgenic Plants Expressing GUS From the LjPLP-IV Promoter

A. Generation of Transgenic Plants

Chimeric gene constructs were prepared using standard molecular biological techniques. Briefly, the 581-bp DNA fragment derived from intron 10 of the LjPLP-IV gene (SEQ ID NO:4) was PCR amplified an cloned in both orientation into the unique BamHI restriction site of the pB1101 (Clonetech) derived binary vector. This resulted in the construction of the p-For and p-Rev binary vectors, carrying the intron sequence in forward (p-For) or reverse (p-Rev) orientation, with respect to the GUS coding region.

The binary vectors were independently transferred into Agrobacterium rhizogenes A4 (Tempe and Casse-Delbart, in Schell and Vasil (eds), *Cell Culture and Somatic Cell Genetics of Plants*, Vol. 6. Academic Press, San Diego, Calif., pp. 25–49 [1989]) by using the freeze-thaw method of Hofgen and Willmitzer (Nuc. Acid. Res., 16:9877 [1988]). Transgenic lotus corniculatus cv. Rodeo plants were generated as previously described (Szabados et al., Plant Cell, 2:973 [1990]; Szczyglowski et al., Plant Cell, 6:317 [1994]).

B. Analysis of GUS Activity

GUS activity in the nodule hand sections and other *L. corniculatus* tissues were analyzed histochemically (Jefferson et al., EMBO J., 6:3901 [1987]; Szczyglowski et al., Plant Cell, 6:317 [1994]) using conditions described by Malamy and Benfey (Development, 124:33 [1997]. Briefly, seedlings were stained for GUS activity for up to 3 days in the following solution: 1× GUS buffer, 20% methanol, 0.5 mg/ml X-Gluc (5-bromo-4-chloro-3-indoyl-β-D-glucuronidase). Staining solution was made fresh from a 10× Gus buffer (1M Tris pH 7.5 containing 29 mg/ml NaCl, 6.6 mg/ml $K_3Fe(CN)_6$) that was stored in darkness for no more that one week. Stained tissues were examined using a Wild Heerburgg M420 stereoscope. The images of stained nodule sections were generated using a Kodak DC 120 digital camera and processed using Adobe Workshop 5.02 software.

GUS staining of hand-cut nodule sections revealed that the intron fragment directed GUS expression only to the central, infected zone, of the nodules. Other plant tissues, including *L. corniculatus* roots, leaves and flowers, showed no cytological staining for GUS activity. The intron sequence was found to be capable of activating the reporter gene expression in an orientation-independent manner. However, in contrast with the p-For reporter gene construct, the p-Rev construct showed a strong histochemical staining also in the nodule vascular bundles. The promoter-less uidA construct, used as a negative control, showed no detectable staining in the central zone of the nodules. However, a relatively weak staining in nodule vascular bundles could be detected in some of these transgenic lines.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, developmental biology, biochemistry, or related fields are intended to be within the scope of the following claims.

We claim:

1. A composition comprising an isolated *Lotus japonicus* PLP-IV promoter nucleic acid, wherein said *Lotus japonicus* PLP-IV promoter nucleic acid has the nucleic acid sequence of SEQ ID NO:4.

2. The composition of claim 1, wherein said promoter is a bi-directional promoter.

3. A vector comprising the composition of claim 1.

4. The vector of claim 3, wherein said promoter is a bi-directional promoter.

5. The vector of claim 3, wherein said promoter is operably linked to a reporter gene.

6. A plant cell transformed with the vector of claim 3.

7. A differentiated dicotyledonous plant comprising the plant cell of claim 6.

8. A differentiated monocotyledonous plant comprising the plant cell of claim 6.

9. A composition comprising an isolated nucleic acid that is at least 95% identical to SEQ ID NO:4, and wherein said nucleic acid directs bidirectional transcription.

10. A composition comprising a vector comprising two nucleic acid sequences in opposite orientation, wherein said two nucleic acid sequences are separated by an isolated *Lotus japonicus* PLP promoter nucleic acid, wherein said *Lotus japonicus* PLP-IV promoter nucleic acid has the nucleic acid sequence of SEQ ID NO:4.

11. The vector of claim 10, wherein said promoter is a bi-directional promoter.

12. The vector of claim 10, wherein said promoter is operably linked to a reporter gene.

13. A plant cell transformed with the vector of claim 10.

14. A differentiated dicotyledonous plant comprising the plant cell of claim 13.

15. A differentiated monocotyledonous plant comprising the plant cell of claim 13.

16. A composition comprising a vector comprising two nucleic acid sequences in opposite orientation, wherein said two nucleic acid sequences are separated by an isolated *Lotus japonicus* PLP promoter nucleic acid, wherein said isolated *Lotus japonicus* PLP promoter nucleic acid is at least 95% identical to SEQ ID NO:4 and wherein said nucleic acid directs bidirectional transcription.

17. A transgenic plant comprising a transgene, wherein said transgene comprises a vector comprising two nucleic acid sequences in opposite orientation, wherein said two nucleic acid sequences are separated by an isolated *Lotus japonicus* PLP promoter nucleic acid sequence, wherein said *Lotus japonicus* PLP-IV promoter nucleic acid has the nucleic acid sequence of SEQ ID NO:4.

18. The transgenic plant of claim 17, wherein said promoter is a bi-directional promoter.

19. The transgenic plant of claim 17, wherein said promoter is operably linked to a reporter gene.

20. A transgenic plant comprising a transgene, wherein said transgene comprises a vector comprising two nucleic acid sequences in opposite orientation, wherein said two nucleic acid sequences are separated by an isolated *Lotus japonicus* PLP promoter nucleic acid, wherein said isolated *Lotus japonicus* PLP promoter nucleic acid is at least 95% identical to SEQ ID NO:4 and wherein said nucleic acid directs bidirectional transcription.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: synthetic

<400> SEQUENCE: 1
caagcaattt gctttgatac                                            20

<210> SEQ ID NO 2
<211> LENGTH: 21
<212> TYPE: DNA
<213> ORGANISM: Artificial Sequence
<220> FEATURE:
<223> OTHER INFORMATION: synthetic

<400> SEQUENCE: 2

```
gggagtgctt tgttctctg c                                                        21

<210> SEQ ID NO 3
<211> LENGTH: 20
<212> TYPE: DNA
<213> ORGANISM: Artificial Sequence
<220> FEATURE:
<223> OTHER INFORMATION: synthetic

<400> SEQUENCE: 3
cttgtcacat aagcaaaagg                                                         20

<210> SEQ ID NO 4
<211> LENGTH: 580
<212> TYPE: DNA
<213> ORGANISM: lotus japonicus

<400> SEQUENCE: 4
gctcagctct cagctgagca caccaaactc cttccctcag ctttctactt atagaagttt             60
gaaatgatcc ttagctaaga tgaagaggca agtgagctcg agctaaggtg aagagtcaag            120
tggcccttgg aggttgggat gattatccaa caattctccc cctctatccc aaacaagaga            180
gagtggcacc tgacatctat catcttgaga tgcccatcct aactatgcct caatatagct            240
ctgagcttct cacaagcgac tatcttcgaa aatatgtctg tttaattctc tcttctagct            300
aacccaaggt cttgaagaaa ccacttcgac cacaatatct cctgccgtag cgtgtactca            360
acttctgttg tggataagct tccaatcttg attgtcatga ctcttattta aggtgaaggg            420
gcaagtgatc cttggagttt gggatggata tccaacaaaa taaacatttt gtatgttcta            480
ttttgtgatt ggattttaga tatggccttc ttcttttgga attctgtgca ctataaagca            540
ggtgttgcgt tgaattttt tctagtttca cttgaccaca                                   580
```